US009060757B2

(12) United States Patent
Lawson et al.

(10) Patent No.: US 9,060,757 B2
(45) Date of Patent: Jun. 23, 2015

(54) DISTRACTOR

(75) Inventors: Jonathan Lawson, Cambridge (GB);
Scott Johnson, Newmarket (GB);
Ernest Corraro, Jr., Bethel, CT (US);
Hanspeter Robert Bayer, Meriden, CT (US); Robert H. Humphries, Jr., Danbury, CT (US)

(73) Assignee: Ranier Limited, Cambridge (GB)

( * ) Notice: Subject to any disclaimer, the term of this patent is extended or adjusted under 35 U.S.C. 154(b) by 1688 days.

(21) Appl. No.: 12/115,043

(22) Filed: May 5, 2008

(65) Prior Publication Data

US 2009/0275952 A1 Nov. 5, 2009

(51) Int. Cl.
| | |
|---|---|
| A61B 17/58 | (2006.01) |
| A61B 17/60 | (2006.01) |
| A61B 17/02 | (2006.01) |
| A61B 17/17 | (2006.01) |
| A61B 17/70 | (2006.01) |
| A61B 17/00 | (2006.01) |
| A61B 19/00 | (2006.01) |

(52) U.S. Cl.
CPC .......... *A61B 17/025* (2013.01); *A61B 17/0206* (2013.01); *A61B 17/1757* (2013.01); *A61B 17/7077* (2013.01); *A61B 2017/0042* (2013.01); *A61B 2017/00915* (2013.01); *A61B 2017/0092* (2013.01); *A61B 2017/0256* (2013.01); *A61B 2019/303* (2013.01); *A61B 2019/4836* (2013.01)

(58) Field of Classification Search
USPC .......... 606/90, 210, 214, 215, 228, 231–233, 606/912
See application file for complete search history.

(56) References Cited

U.S. PATENT DOCUMENTS

| | | | | |
|---|---|---|---|---|
| 2,670,732 | A | * | 3/1954 | Nelson .......................... 600/234 |
| 4,143,652 | A | * | 3/1979 | Meier et al. ................... 600/203 |
| 4,573,452 | A | * | 3/1986 | Greenberg .................... 600/102 |

(Continued)

FOREIGN PATENT DOCUMENTS

| | | |
|---|---|---|
| EP | 0749724 A | 12/1996 |
| JP | 09-015975 | 7/1998 |

(Continued)

OTHER PUBLICATIONS

International Search Report for Application No. PCT/US2009/002747 mailed Jul. 10, 2009.

(Continued)

*Primary Examiner* — Christian Sevilla
(74) *Attorney, Agent, or Firm* — Wolf, Greenfield & Sacks, P.C.

(57) ABSTRACT

An instrument for distracting and/or compressing adjacent vertebrae is described. The instrument includes a yoke, a first blade movably mounted to the yoke, a second blade mounted to the yoke and an adjustment system. The yoke, the first blade and the second blade form a working channel for the instrument. The adjustment system of the instrument is configured to adjust a spacing between the first blade and the second blade by selectively moving the first blade relative to the second blade to distract and/or compress adjacent vertebrae when the first blade and the second blade have been secured to the adjacent vertebrae. The instrument may include a depth stop system that limits an insertion depth of an associated tool inserted into the working channel of the instrument. The adjustable depth stop system includes a releasable catch for securing a stop element of the associated tool. A position of the releasable catch relative to the working channel is adjustable to vary the insertion depth of the associated tool.

23 Claims, 8 Drawing Sheets

(56) References Cited

U.S. PATENT DOCUMENTS

| | | | |
|---|---|---|---|
| 4,852,552 A * | 8/1989 | Chaux | 600/232 |
| 4,898,161 A | 2/1990 | Grundei | |
| 5,059,194 A | 10/1991 | Michelson | |
| 5,231,974 A * | 8/1993 | Giglio et al. | 600/206 |
| 5,662,300 A * | 9/1997 | Michelson | 248/279.1 |
| 5,697,939 A * | 12/1997 | Kubota et al. | 606/130 |
| 5,728,046 A * | 3/1998 | Mayer et al. | 600/210 |
| 5,928,139 A * | 7/1999 | Koros et al. | 600/205 |
| 5,931,777 A | 8/1999 | Sava | |
| 5,944,658 A | 8/1999 | Koros et al. | |
| 6,102,853 A * | 8/2000 | Scirica et al. | 600/227 |
| 6,139,493 A | 10/2000 | Koros et al. | |
| 6,331,158 B1 * | 12/2001 | Hu et al. | 600/232 |
| 6,814,737 B2 | 11/2004 | Cauthen | |
| 7,004,947 B2 | 2/2006 | Shluzas et al. | |
| 7,189,234 B2 | 3/2007 | Zucherman et al. | |
| 2004/0225295 A1 | 11/2004 | Zubok et al. | |
| 2005/0021040 A1 * | 1/2005 | Bertagnoli | 606/90 |
| 2005/0075643 A1 | 4/2005 | Schwab et al. | |
| 2005/0143747 A1 | 6/2005 | Zubok et al. | |
| 2005/0203533 A1 | 9/2005 | Ferguson et al. | |
| 2006/0004398 A1 * | 1/2006 | Binder et al. | 606/191 |
| 2006/0009777 A1 | 1/2006 | Lim et al. | |
| 2006/0052672 A1 | 3/2006 | Landry et al. | |
| 2006/0084844 A1 | 4/2006 | Nehls | |
| 2006/0241642 A1 | 10/2006 | Arnin et al. | |
| 2006/0271096 A1 * | 11/2006 | Hamada | 606/198 |
| 2007/0073111 A1 * | 3/2007 | Bass | 600/215 |
| 2007/0123903 A1 | 5/2007 | Raymond et al. | |
| 2007/0123904 A1 | 5/2007 | Stad et al. | |
| 2007/0123985 A1 | 5/2007 | Errico et al. | |
| 2007/0185375 A1 | 8/2007 | Stad et al. | |
| 2007/0191856 A1 | 8/2007 | Gil et al. | |
| 2007/0191857 A1 | 8/2007 | Allard et al. | |
| 2007/0233153 A1 | 10/2007 | Shipp et al. | |
| 2007/0276188 A1 * | 11/2007 | Chappuis | 600/202 |
| 2007/0282171 A1 | 12/2007 | Karpowicz et al. | |
| 2008/0009863 A1 | 1/2008 | Bond et al. | |
| 2008/0058606 A1 | 3/2008 | Miles et al. | |
| 2009/0036746 A1 * | 2/2009 | Blackwell et al. | 600/219 |
| 2009/0216239 A1 | 8/2009 | Johansson et al. | |

FOREIGN PATENT DOCUMENTS

| | | |
|---|---|---|
| WO | WO 2005/060613 A | 7/2005 |
| WO | WO 2007/074295 A1 | 7/2007 |

OTHER PUBLICATIONS

Mayer, H.M. ed. Minimally Invasive Spine Surgery: A Surgical Manual, $2^{nd}$ ed., 2006, (summary only), http://www.springer.com/east/home/medicine/orthopedics?SGWID=5-10075-22-4620543 . . . (retrieved Jan. 22, 2008).

Sekhon, LH, Ball JR, Artificial Cervical Disc Replacement: Principles, Types and Techniques, Neurol India, Dec. 2005 53(4): 445-50, (abstract only), (retrieved Jan. 22, 2008).

Anterior Cervical Fusion (ACF) Instruments Technique Guide, Synthes Spine, 16 pages, http://products.synthes.com/prod_support/Product%20Support%20Materials/Technique%20Guides/SPINE/SPTGACF32509F.pdf, copyright 1999, (retrieved Aug. 4, 2009).

International Search Report for Application No. PCT/US2009/002747 mailed Dec. 11, 2009.

* cited by examiner

DISTRACTOR

RELATED APPLICATIONS

This application is related to co-pending U.S. patent application Ser. No. 12/115,054 entitled "ENDPLATE PREPARATION INSTRUMENT," and filed on the same day as this application, which is herein incorporated by reference in its entirety.

FIELD OF INVENTION

The present invention relates to an instrument for distracting and/or compressing adjacent vertebrae.

BACKGROUND

A spinal disc lies between endplates of adjacent vertebrae. The disc stabilizes the spine and assists in distributing forces between vertebral bodies. A spinal disc may be displaced or damaged due to trauma, disease or other degenerative processes that can occur over time. For example, a portion of the disk may weaken or tear which can result in the protrusion of the nucleus pulposus into a region of the spine (e.g., the vertebratal foramen) that includes spinal nerves. The protruding nucleus pulposus may press against spinal nerves causing pain, numbness, tingling, diminished strength and/or a loss of motion. Another common degenerative process is the loss of fluid from the disc. Such fluid loss can limit the ability of the disc to absorb stress and may reduce its height, which can lead to further instability of the spine, as well as decreasing mobility and causing pain.

To address the conditions described above, a displaced or damaged spinal disc may be surgically removed from the spine. Historically, after the disc is removed, a fusing implant is inserted into the disc space that allows the two adjacent vertebrae to fuse together. In other surgical procedures, the damaged disc is removed and replaced with an artificial disc. Specialized instruments have been provided to permit access to the disc space and to distract or compress adjacent vertebrae.

SUMMARY

Aspects of the invention relate to an instrument for distracting and/or compressing adjacent vertebrae. The instrument includes a yoke, a first blade movably mounted to the yoke and a second blade mounted to the yoke and opposed to the first blade. The first blade, the second blade and the yoke form a working channel of the instrument. The instrument also includes an adjustment system configured to adjust a spacing between the first blade and the second blade by selectively moving the first blade relative to the second blade. When adjacent vertebrae are secured to the first blade and the second blade, selectively moving the first blade relative to the second blade distracts or compresses the adjacent vertebrae.

Other aspects of the invention relate to an instrument for distracting and/or compressing adjacent vertebrae that includes a first blade, a second blade and a depth stop system. A working channel is located between the first blade and the second blade. A spacing between the first blade and the second blade is selectively adjustable. The depth stop system limits the insertion depth of an associated tool inserted into the working channel. The depth stop system includes a releasable catch for securing a stop element of the associated tool. The position of the releasable catch relative to the working channel is adjustable to vary the depth of the associated tool.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1A:
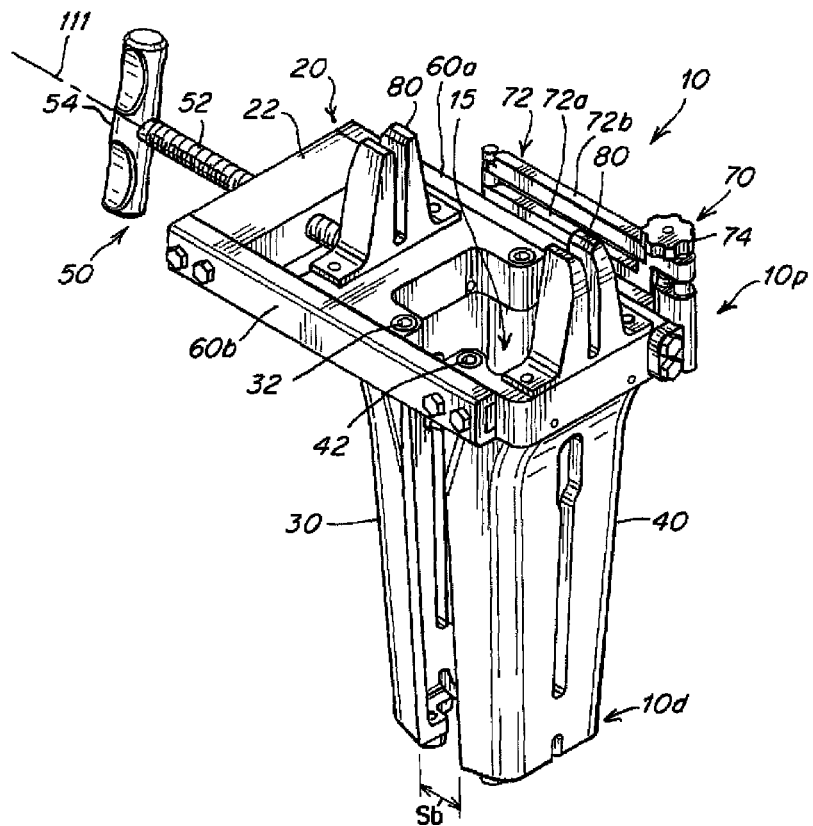
FIG. 1A is perspective view of an instrument for distracting and/or compressing adjacent vertebrae, in accordance with an illustrative embodiment of the invention.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting.

Aspects of the invention relate to an instrument for distracting and/or compressing adjacent vertebrae and a method of manipulating vertebrae in a spinal surgery. Some exemplary embodiments include an instrument with a yoke, a first blade, a second blade, and an adjustment system. The first blade is movably mounted to the yoke. The second blade is mounted to the yoke and opposed to the first blade. The yoke, the first blade and the second blade form a working channel for the instrument. The adjustment system of the instrument is configured to adjust a spacing between the first blade and the second blade by selectively moving the first blade relative to the second blade to distract and/or compress adjacent vertebrae when the first blade and the second blade have been secured to the adjacent vertebrae.

In some embodiments, the first blade may be slidably mounted to the yoke. In some embodiments, the second blade is movably mounted to the yoke, and in other embodiments, the second blade is fixed relative to the yoke. In some embodiments, the yoke includes a pair of opposed guideways that each support the first blade and the second blade. Each of the first blade and the second blade may be disposed between the opposed guideways. In some embodiments, the adjustment system may connect to a central portion of the first blade between the opposed guide ways. The adjustment system may exert a force on the central portion of the first blade between the opposed guide ways to change a separation between the first blade and the second blade.

Other exemplary embodiments include an instrument for distracting and/or compressing vertebra having a depth stop system. The instrument includes a first blade and a second blade with a working channel of the instrument between the first and second blades. Changing a spacing between the first blade and the second blade changes a spacing of adjacent vertebrae secured to the first blade and the second blade.

The depth stop system limits an insertion depth of an associated tool inserted into the working channel of the instrument. The adjustable depth stop system includes a releasable catch for securing a stop element of the associated tool. The position of the releasable catch relative to the working channel is adjustable to vary the insertion depth of the associated tool. The releasable catch may include a distal catch portion that engages a stop element of the associated tool to block further insertion of the tool. The releasable catch may also include a proximal catch portion that prevents the tool from being withdrawn from the working channel when the proximal catch portion is closed over the stop element of the tool. The depth stop system may also include a depth selection element configured to change a position of the releasable catch relative to the working channel.

In some embodiments, a distal portion of the first blade and a distal portion of the second blade may be configured to anchor the instrument to bone. The first blade may include at least one channel extending from a proximal portion of the first blade to a distal portion of the first blade that is configured to receive a spinal fixation element for anchoring the first blade to bone. In some embodiments, portions of the instrument comprise radiolucent material.

Some embodiments provide a method of compressing and distracting using the instrument. The method also includes using a tool inserted into a working channel of the instrument to treat the adjacent vertebrae.

Figure 1B:
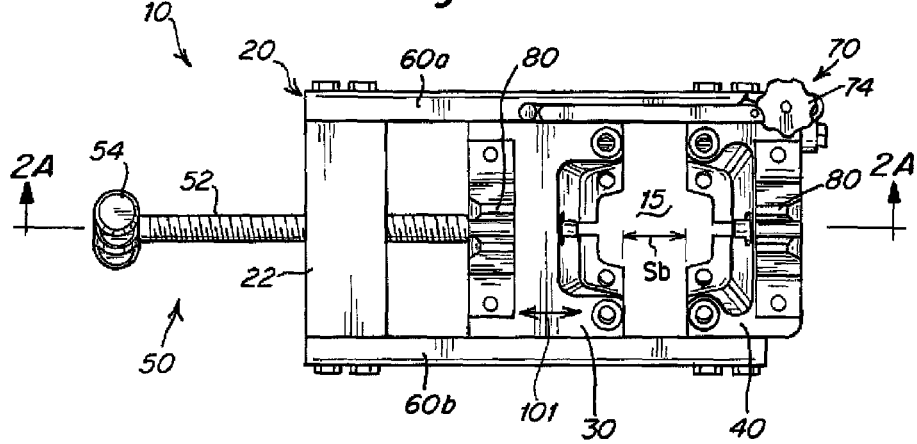
FIG. 1B is a top view of the instrument depicted in FIG. 1A.

Turning to FIGS. 1A, and 1B, an instrument 10 for compression and/or distraction of adjacent vertebrae is depicted. As shown by the perspective view of FIG. 1A, the instrument 10 includes a yoke 20, a first blade 30 movably mounted to the yoke 20, and a second blade 40 mounted to the yoke 20 and opposed to the first blade 30. The first blade 30, the second blade 40 and the yoke 20 form a working channel 15 as shown by the top view of FIG. 1B. The instrument 10 also includes an adjustment system 50 configured to adjust a spacing $S_b$ between the first blade 30 and the second blade 40 by selectively moving the first blade 30 relative to the second blade 40 as indicated by arrow 101. When the first blade 30 and the second blade 50 are secured to adjacent vertebrae, adjusting the spacing $S_b$ between the first blade 30 and the second blade 40 compresses or distracts the adjacent vertebrae.

In some embodiments, the yoke 20 includes a pair of opposed guideways 60a, 60b. The opposed guideways 60a, 60b may support both the first blade 30 and the second blade 40, which are disposed between the opposed guideways 60a, 60b. A central portion of the yoke 22 may connect the opposed guideways 60a, 60b. The second blade 40 may also fixedly connect and support the opposed guideways 60a, 60b. Further details regarding movably mounting the first blade 30 on the yoke 20 are described below with respect to FIGS. 3A and 3B.

The adjustment system 50 may couple with the first blade 30 between the opposed guideways 60a, 60b to exert a force on the first blade 30. The adjustment system 50 may include a drive element 52 that exerts the force on the first blade 30. The adjustment system 50 may include a handle 54 connected with the drive element 52 that allows a user to manually control the adjustment system 50. Further details regarding embodiments of the adjustment system 50 are described below with respect to FIGS. 2A and 2B.

In some embodiments of the invention, the instrument 10 includes a depth stop system 70 configured to limit an insertion depth for an associated tool inserted into the working channel 15 of the instrument 10. The depth stop system 70 includes a releasable catch 72. The releasable catch 72 secures a stop element of the associated tool. The position of the releasable catch 72 is adjustable to vary the insertion depth of the associated tool. The releasable catch 72 may include a distal catch portion 72a and a proximal catch portion 72b. The distal catch portion 72a of the instrument 10 prevents the associated tool from being inserted further into the working channel 15. When the depth element is secured in the releasable catch 72, the proximal catch portion 72b prevents the associated tool from being withdrawn from the working channel 15

Some embodiments of the invention include one or more alignment elements 80 configured to engage corresponding alignment protrusions of an associated tool inserted into the working channel 15 of the instrument 10. The one or more alignment elements 80 may reduce or prevent rotation of the tool relative to the instrument 10 when the tool alignment protrusions are engaged by the instrument alignment elements 80. Further details regarding the depth stop system 70 and tool alignment elements 80 are described below with respect to FIGS. 4A-5B.

As described above, the first blade 30 may be secured to a vertebra and the second blade 40 may be secured to an adjacent vertebrae. Any suitable method may be used to secure the first blade 30 and the second blade 40 to adjacent vertebrae. In some embodiments, the instrument 10 may be mounted to spinal fixation elements previously attached to the adjacent vertebrae. In other embodiments, spinal fixation elements may be attached to the adjacent vertebrae through the instrument 10 or using the instrument 10. Securing the spinal fixation elements to adjacent vertebrae and securing the instrument 10 to the adjacent vertebrae may occur separately or simultaneously.

Figure 1C:
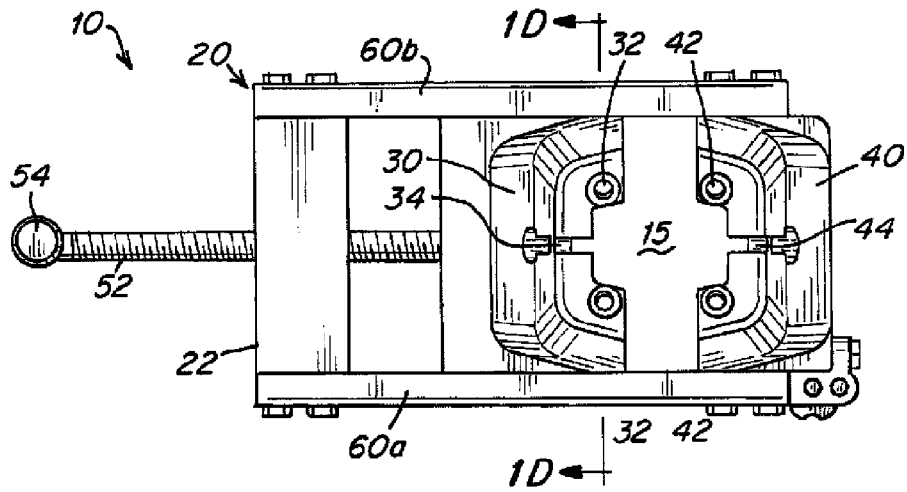
FIG. 1C is a bottom view of the instrument depicted in FIGS. 1A and 1B.
Figure 1D:
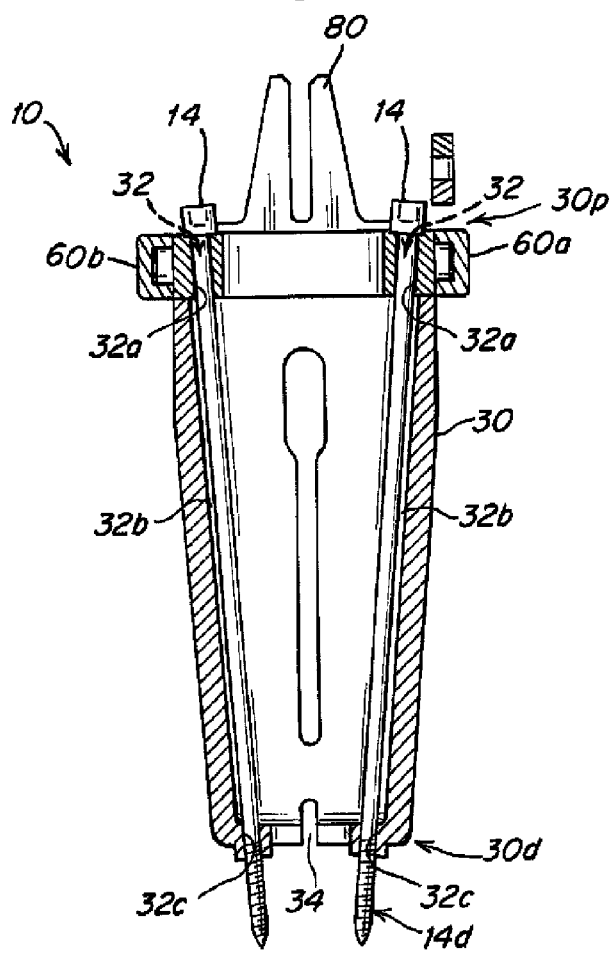
FIG. 1D is a cross-sectional view taken along line 1D-1D of FIG. 1C, but with spinal fixation elements extending through channels of the instrument, in accordance with aspects of the invention.

For example, instrument 10 may include one or more channels 32, 42 each configured to receive a spinal fixation element 14 for anchoring the instrument 10 to bone, such as a bone screw as shown in FIGS. 1C and 1D. Channels 32 may be formed in the first blade 30 and/or channels 42 may be formed in the second blade 40 of the instrument 10, according to some embodiments of the invention. Although attributes and aspects of exemplary channels configured to receive spinal fixation elements will be described with respect to channels 32 of the first blade 30, any attributes and properties described with respect to the channels 32 of the first blade 30 may be incorporated into channels 42 of the second blade 40, as the invention is not limited in this respect.

FIG. 1C shows a bottom view of the instrument depicted in FIGS. 1A and 1B. FIG. 1D depicts a cross-sectional view of the instrument 10 taken along line 1D-1D of FIG. 1C with spinal fixation elements 14 inserted into the channels 32, 42. Channels 32 may extend to a distal portion of the first blade 30$d$. Channel 32 may be closed along its entire length, or may include multiple coaxial closed channels separated by one or more coaxial open areas. As depicted in FIG. 1D, each channel 32 includes a closed channel 32$a$ in a proximal portion of the first blade 30$p$, and a closed channel 32$e$ in the distal portion of the closed blade 30$d$ separated by an open area 32$b$. Each spinal fixation element 14 is inserted into a channel 32. A distal portion of the spinal fixation element 14$d$ exits from a distal portion 30$d$ of the first blade to engage bone.

In some embodiments, the first blade 30 and/or the second blade 40 may include one or more marker engaging elements for engaging bone markers. In the depicted embodiment, the first blade 30 and the second blade 40 each include a slot 34, 44 for engaging a marker that is secured to a vertebra.

Figure 2A:
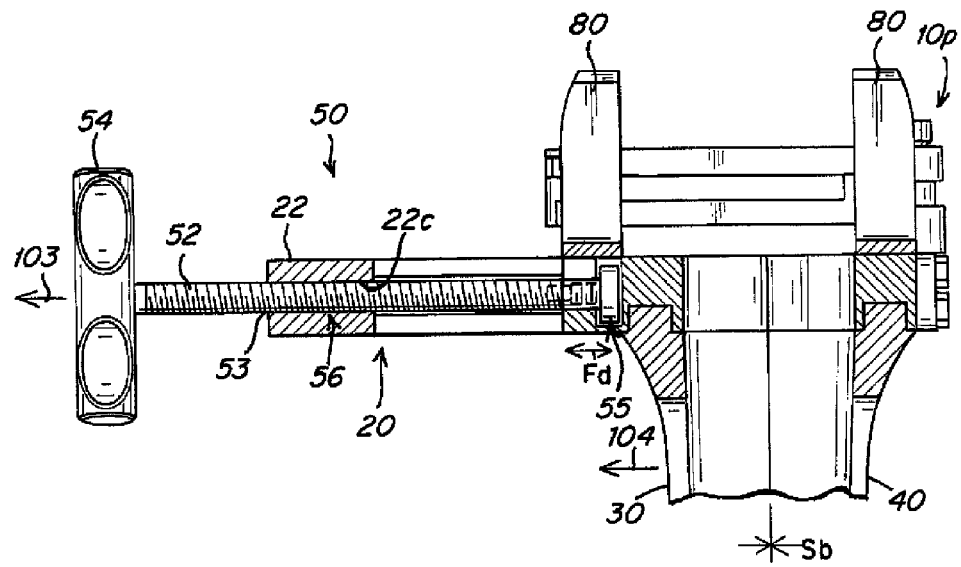
FIG. 2A is a side cross-sectional side view taken along line 2A-2A of FIG. 1B in accordance with some embodiments of the invention.
Figure 2B:
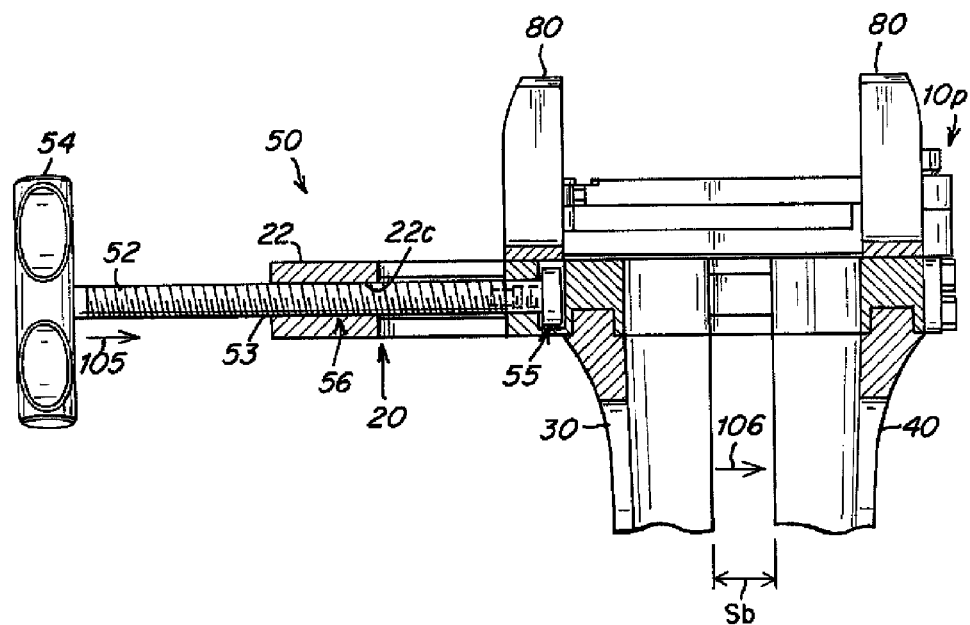
FIG. 2B is a side cross-sectional view of the instrument with a first blade separated from a second blade.

FIGS. 2A and 2B further illustrate the adjustment system 50 configured to adjust a spacing $S_b$ between the first blade 30 and the second blade 40, according to aspects of an illustrative embodiment. FIGS. 2A and 2B show cross-sectional views of a proximal portion of the instrument 10$p$ with a cross-section taken at line 2A-2A of FIG. 1B. The system 50 includes a drive element 52 that is coupled with the first blade 30 by a blade-drive coupling 55. The drive element 52 is configured to exert a force $F_d$ on the first blade 30. Force $F_d$ exerted on the drive element 52 is transmitted to the first blade 30 through the blade-drive coupling 55, moving the first blade 30 with respect to the second blade 40 to change the blade separation $S_b$. The drive element 52 may also be coupled with a central portion of the yoke 22 by a yoke-drive coupling 56.

In some embodiments, rotation of the drive element 52 may cause a change in blade separation $S_b$. The blade-drive coupling 55 may be a rotatable coupling that transmits linear force from the drive element 52 to the first blade 30 while allowing the drive element 55 to freely rotate along its axis with respect to the first blade 30. The drive element 52 may have one or more threads 53. The yoke-drive coupling 56 may include a threaded channel 22$c$ of the central portion of the yoke 22 that engages the threads 53 of the drive element 52.

Handle 54 may be used to rotate drive element 52. Although handle 54 is depicted disposed away from the working channel 15 and extending parallel to the opposed guideways 60$a$, 60$b$, in other embodiments, the handle 54 may be have a different location and/or a different orientation as the invention is not limited in this respect. For example, the handle 54 may be proximal to the working channel 15. The handle 54 may have any location that facilitates access for a surgeon, or a location of a handle may be selected for any other reason.

In some embodiments, handle 54 may be rotated about an axis 111 that is substantially parallel to the opposed guideways 60$a$, 60$b$. In other embodiments, the handle 54 and/or the drive element 52 may include a coupling that allows the handle 54 to be rotated about an axis that is not parallel to the opposed guideways 60$a$, 60$b$. For example, in some embodiments, the handle 54 may be rotated about an axis that is substantially parallel to the working channel 15 of the instrument. An exemplary instrument including a handle 54 with an adjustable orientation is described below with respect to FIGS. 6A and 6B.

If drive element 52 has "right handed" threading, rotating drive element 52 counter-clockwise with respect to the yoke 20 exerts a force on the yoke 20 to displace the drive element 52 with respect to the yoke as indicated by arrow 103 in FIG. 2A. As the drive element 52 is displaced relative to the yoke 20, the first blade 30 is also displaced relative to the yoke 30 due to the blade-drive coupling 55 as indicated by arrow 104 in FIG. 2A.

FIG. 2B shows the proximal instrument portion 10$p$ after the drive element 54 and the first blade 30 have been displaced relative to yoke 20. In the depicted embodiment, the second blade 40 does not move with respect to the yoke 20, meaning that the first blade 30 has been displaced with respect to the second blade 40 increasing the blade separation $S_b$. If the first blade 30 and second blade 40 are anchored to adjacent vertebrae, the increase in blade separation $S_b$ distracts the vertebra.

If the drive element 52 is rotated clockwise with respect to the yoke 20, the drive element 52 will be displaced with respect to the yoke 20 as indicated by arrow 105. Displacement of the drive element 52 displaces the first blade 30, which is coupled with the drive element 52, as indicated by arrow 106. The resulting decrease in blade separation $S_d$ distracts the adjacent vertebrae. Although the adjustment system 50 uses rotational motion and a threaded drive element 52 to change blade spacing, other embodiments of the invention may employ other suitable configurations of an adjustment system 50 as the invention is not limited in this respect.

Figure 3A:
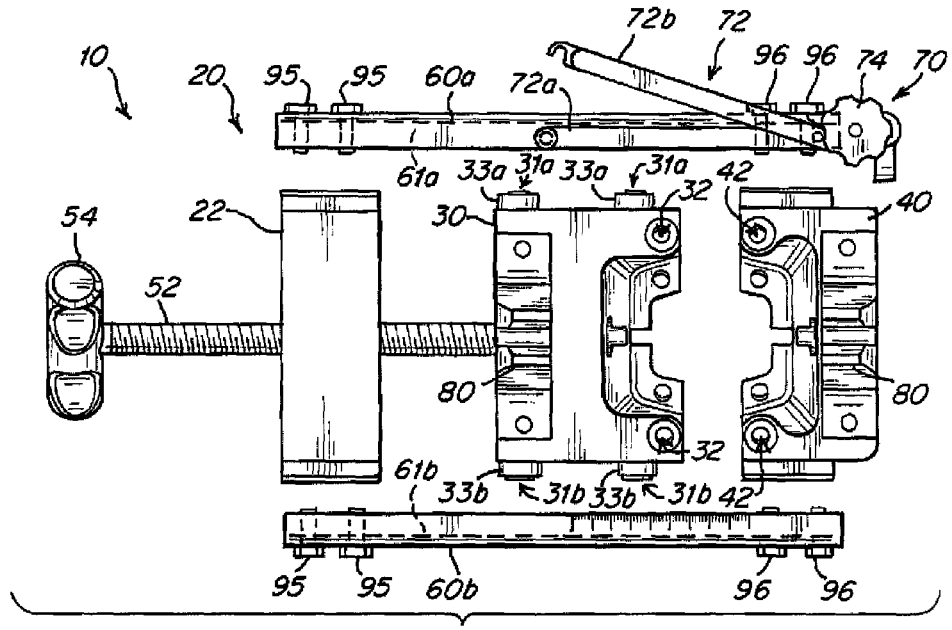
FIG. 3A is an exploded top view of the instrument, in accordance with some embodiments of the invention.
Figure 3B:
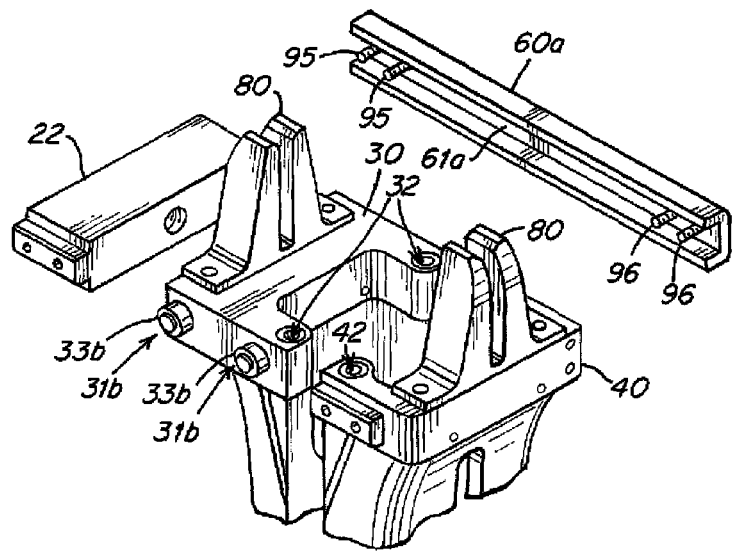
FIG. 3B is an exploded perspective view of parts of the instrument.

FIGS. 3A and 3B further illustrate details of the mounting of the first blade 30 and the second blade 50 to the yoke 20, according to some embodiments of the invention. FIG. 3A depicts a top exploded view of instrument 10 showing opposed guideways 60$a$, 60$b$ separated from the first blade 30, the second blade 40 and the central yoke portion 22. FIG. 3B depicts a perspective exploded view of the first blade 30, the second blade 40, the central yoke portion 22, and one of the opposed guideways 60$a$. Other elements of the instrument 10 have been omitted from FIG. 3B for clarity.

The central yoke portion 22 is attached to the opposed guideways 60$a$, 60$b$ forming the yoke 20. As depicted, the opposed guideways 60$a$, 60$b$ are attached to the central yoke portion 22 using screws 95. However, the opposed guideways 60$a$, 60$b$ may be attached to the central yoke portion 22 using any suitable techniques or elements. In other embodiments, the opposed guideways 60$a$, 60$b$ may be integral with the central yoke portion 22, as the invention is not limited in this regard.

In some embodiments, the second blade 40 is fixedly mounted to the yoke 20. For example, the second blade 40 may be attached to the opposed guideways 60$a$, 60$b$ using screws 96, as depicted. However, the second blade 40 may be attached to the opposed guideways 60$a$, 60$b$ using any suitable techniques or elements. In other embodiments, the second blade 40 may be movably mounted to the opposed guideways 60$a$, 60$b$, as the invention is not limited in this regard.

As described above, the first blade 30 is movably mounted to the yoke 20. In some embodiments, the first blade 30 is slidably mounted to the yoke 20. For example, opposed guideways 60$a$, 60$b$ may include channels 61$a$, 61$b$. The first blade 30 may have projections 31$a$, 31$b$, which extend into channels 61$a$, 61$b$ of the opposed guideways 60$a$, 60$b$ when the opposed guideways 60$a$, 60$b$ are attached to the central yoke portion 22. The channels 61$a$, 61$b$ limit movement of the first blade 30 to movement in a direction parallel to channels 61$a$, 61$b$. The projections 31$a$, 31$b$ may includes bearings 33a, 33b, which reduce sliding friction between the protrusions 31a, 31b of the first blade 30, and the channels 60a, 60b of the of the opposed guideways 60a, 60b. Although the depicted embodiment includes projections 31a and 31b on the first blade 30 and corresponding channels 61a and 61b of the yoke 20, in other embodiments, the yoke 20 may include projections and the first blade 30 may include corresponding channels. Other suitable techniques and elements may be used to movably mount the first blade 30 to the yoke 20, as the invention is not limited in this respect.

Figure 4A:
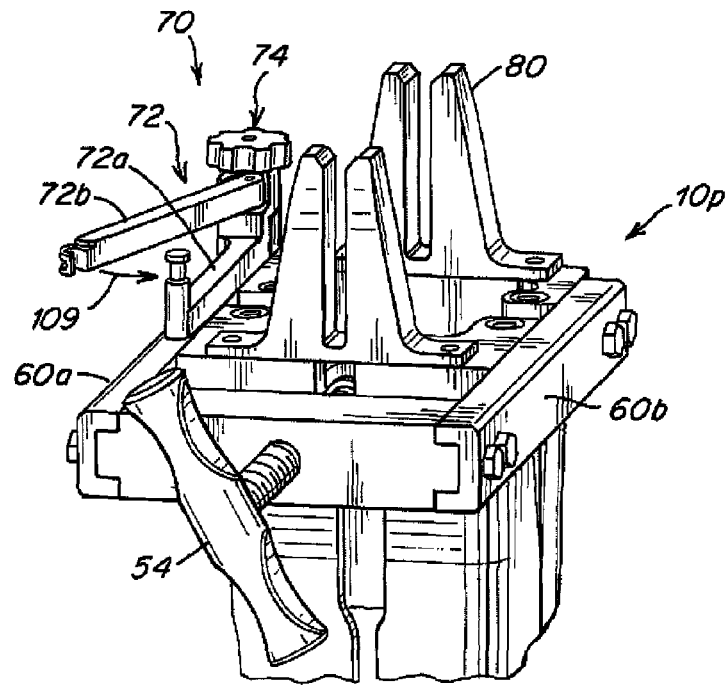
FIG. 4A is a perspective view of a proximal portion of the instrument with a releasable catch of a depth stop system in an open configuration, in accordance with some embodiments of the invention.
Figure 4B:
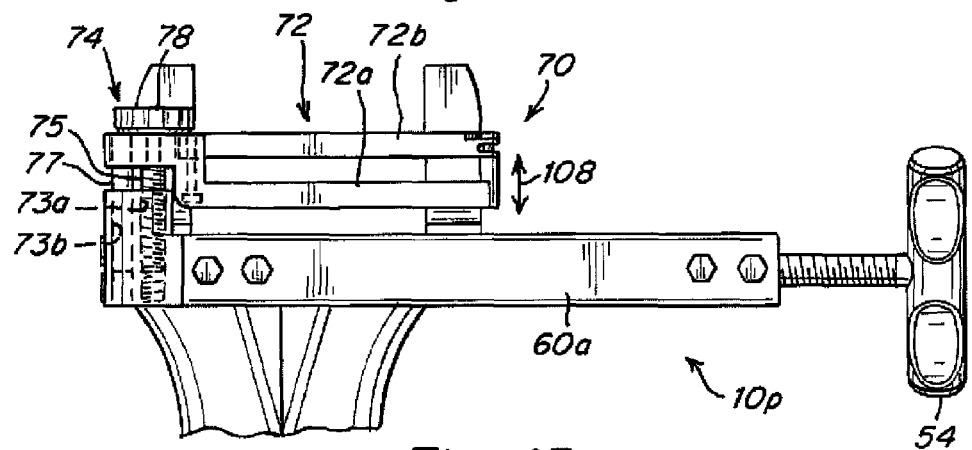
FIG. 4B is a side view of a proximal portion of the instrument showing the depth stop system releasable catch in a closed (engaged) configuration.
Figure 4C:
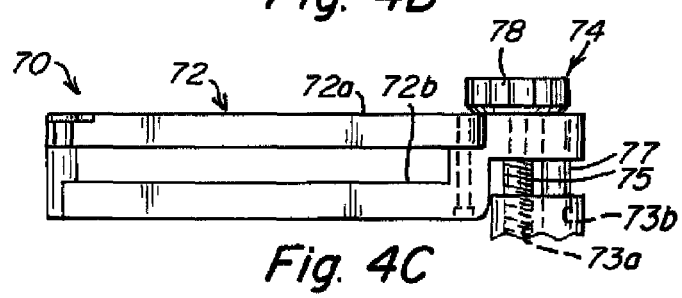
FIG. 4C is side view of an opposite side of the depth stop system.

FIG. 3A shows the depth stop system 70 attached to one of the guideways 60a. The depth stop system 70 may be attached to one or both of the opposed guideways 60a, 60b, the second blade 40, or any other portion of the instrument 10 that does not move with the first blade 30. The depth stop system 70 includes a releasable catch, which may include a proximal catch portion 72b and a distal catch portion 72a. As depicted, the proximal catch portion 72b of the adjustable depth stop system 70 is in an open configuration. FIGS. 4A-4C, further illustrate the depth stop system 70, in accordance with some embodiments of the invention. FIG. 4A depicts a perspective view and FIG. 4B depicts a side view of a proximal portion of the instrument 10p. FIG. 4B shows one side of the depth stop system 70 and FIG. 4C shows the opposite side of the depth stop system 70.

As described above, the depth stop system 70 limits an insertion depth for an associated tool inserted into the working channel 15 of the instrument. The depth stop system 70 includes releasable catch 72 having a distal catch portion 72a, which contacts a corresponding stop element of the tool to physically block the tool from being inserted further into the working channel 15 of the instrument 10. The releasable catch also includes a proximal catch portion 72b that prevents the tool from being withdrawn from the working channel when it is closed over the stop element of the tool.

A position of the releasable catch 72 can be adjusted using the catch adjustment element 74. In some embodiments, a threaded channel 73a of guideway 60a couples with a threaded portion 75 of the catch adjustment element 74. The distal catch portion 72a includes a stationary pin 77 that slidably couples with a channel 73b of guideway 60a. Rotating a knob 78 of the catch adjustment element 74 rotates the threaded portion 75 of the catch adjustment element 74. The stationary pin 77 prevents the distal catch portion 72a from rotating with the threaded portion 75, causing the releasable catch 72 to raise or lower as indicated by arrow 108.

The depth stop system 70 also includes a proximal catch portion 72b. When the proximal catch portion 72b is in an open configuration, as shown in FIG. 4A, an associated tool may be inserted into the working channel 15 of the instrument until the stop element of the tool is engaged and blocked by the distal catch portion 72a of the instrument 10. After the stop element of the associated tool is engaged by the distal catch portion 72a, the proximal catch portion 72b may be moved into a closed configuration, as shown in FIGS. 4B and 4C, which prevents the tool from being withdrawn from the working channel 15. In some embodiments, the proximal catch portion 72b may be rotated from an open configuration to a closed configuration as shown by arrow 109 in FIG. 4A. In other embodiments, the proximal catch portion 72b may pivot between an open configuration and a closed configuration.

In some embodiments, the proximal catch portion 72b and the distal catch portion 72a may engage each other with a temporary coupling to secure the releasable catch 72 in a closed configuration. Examples of such temporary couplings include but are not limited to: interference fittings, fittings that employ detents, snap fit couplings, other quick-release type couplings, etc.

The depth stop system 70 may include a depth stop lock configured to maintain a position of the distal catch portion 72a relative to the working channel 15. The depth stop lock may include a ratchet or a spring capture element. The depth stop lock may include a "thumb lock" or other element that prevents rotation of the knob 78. The depth stop lock may include a cam release. Other suitable elements and techniques for temporarily preventing adjustment of the proximal catch portion 72 will be apparent to one of skill in the art.

Figure 5A:
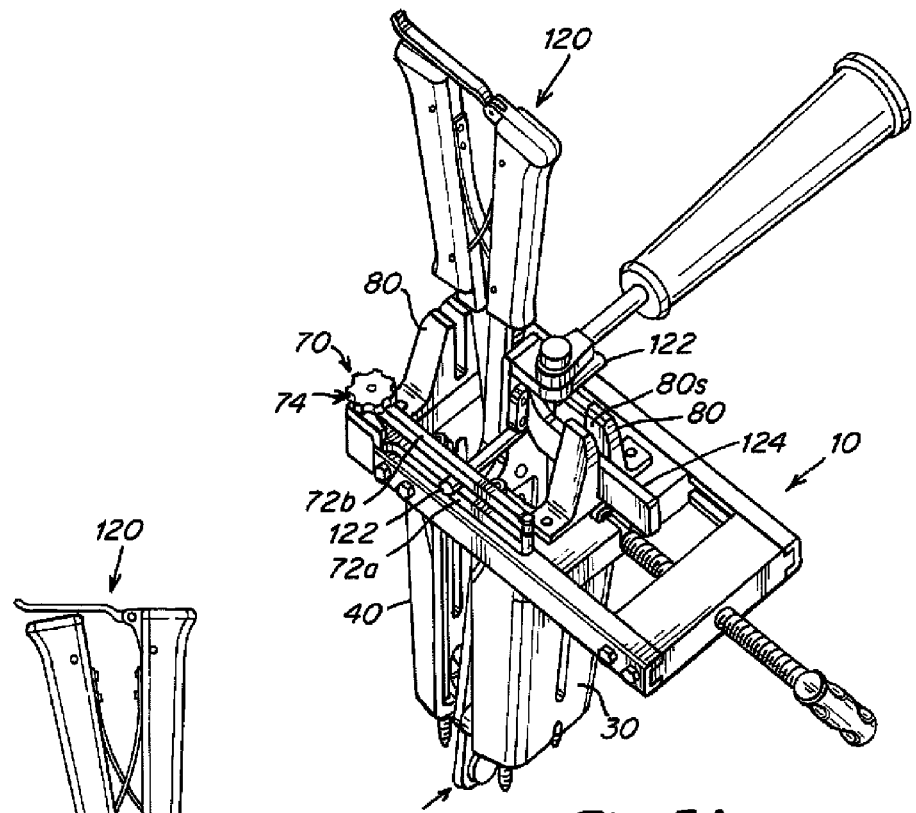
FIG. 5A is a perspective view of an associated tool that is inserted into a working channel of the instrument, according to some aspects of the invention.
Figure 5B:
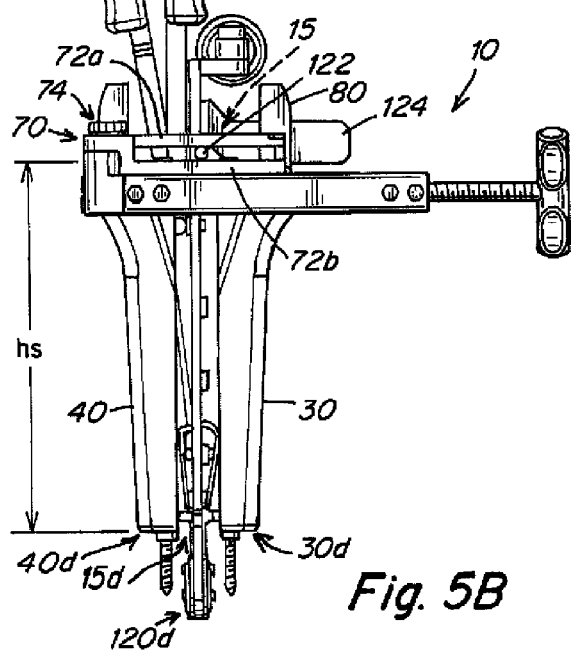
FIG. 5B is a side view of the tool and instrument depicted in FIG. 5A.

FIGS. 5A and 5B, which depict an associated tool 120 inserted into the working channel 15 of the instrument 10, further illustrate the depth stop system 50 and alignment elements 80, in accordance with some embodiments of the invention. Tool 120 has been inserted until a stop element of the tool 122 is in contact with the distal catch portion 72a of the instrument. The stop element of the tool 122 is separated from a distal portion of the working channel 15 of the instrument by a selected height $h_s$. The catch adjustment element 74 can be used to change the selected height $h_s$ by changing a distance between the distal catch portion 72a and the distal portion of the channel 15d, thereby changing an insertion depth limit for the associate tool 122. The proximal catch portion 72b has been moved into a closed configuration, which prevents the tool 120 from being withdrawn from the working channel 15 of the instrument 10.

The tool 120 also includes an alignment protrusion 124 that is engaged by one or more alignment elements 80 of the instrument 10. The alignment elements 80 both align the tool 120 with respect to the instrument 10 and prevent the tool 120 from pivoting or rotating with respect to the instrument 10. The alignment protrusion 120 of the tool may be an alignment blade of alignment keel, and an alignment element 80 of the instrument may include a slot 80s configured to receive the alignment blade or alignment keel, as depicted. Other suitable coordinating tool alignment protrusions and instrument tool alignment elements may be employed, as the present invention is not limited in this respect.

Further details regarding the depicted tool, an endplate preparation tool, may be found in a related copending application entitled "ENDPLATE PREPARATION INSTRUMENT" filed on the same day as this application, the entirety of which is herein incorporated by reference. The depth stop system 70 and the one or more alignment elements 80 of the instrument 100 may engage many different types, sizes and configurations of tools inserted through the working channel 15, as the present invention is not limited in this respect.

Figure 6A:
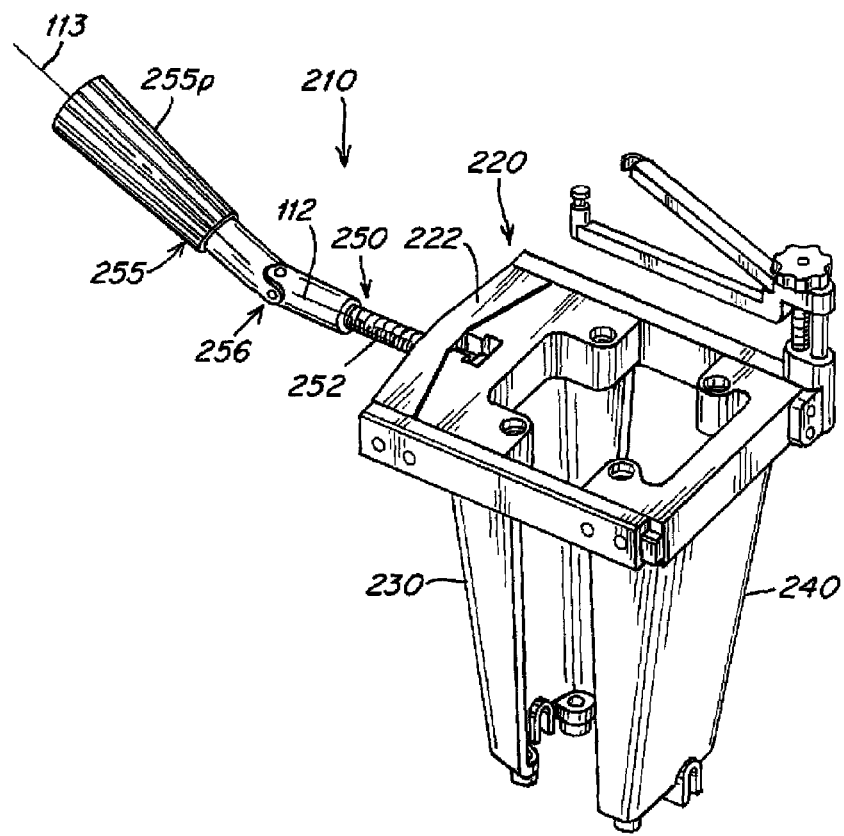
FIG. 6A is a perspective view of an instrument comprising radiolucent material and an adjustment handle with a variable orientation, in accordance with another embodiment of the invention.
Figure 6B:
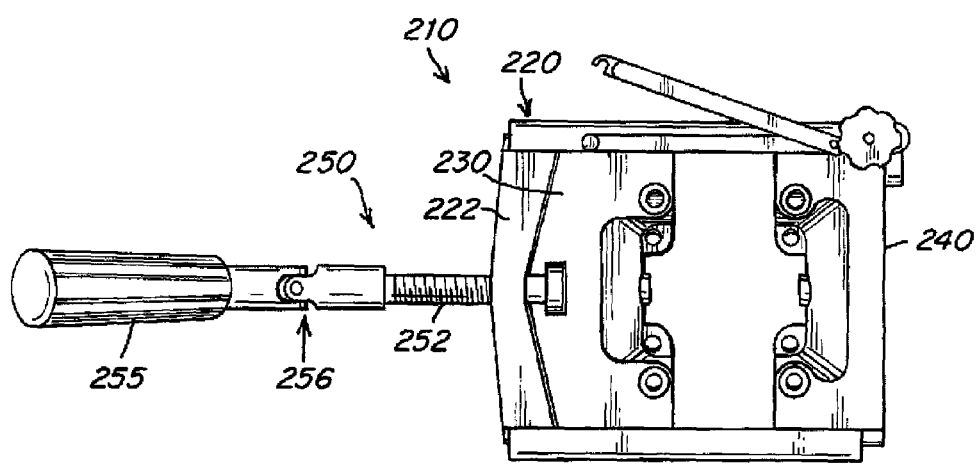
FIG. 6B is a top view of the instrument depicted in FIG. 6A.

FIGS. 6A and 6B show an instrument 210 that includes radiolucent material and a handle with an adjustable orientation, according to other aspects of the invention. An instrument mostly made of a radio-opaque material, such as a metal, may substantially interfere with X-ray imaging of tools, spinal fixation elements and vertebra during surgery. By using a radiolucent material for some portions of the instrument, interference with X-ray imaging may be greatly reduced. Examples of radiolucent materials include, but are not limited to fiber reinforced polymer composites (e.g. glass fiber, carbon fiber), epoxy, polyether-ether-ketone (PEEK), etc. As depicted, a central portion 222 of the yoke 220, a portion of a first blade 230, and a portion of a second blade 240 of the instrument 210 include a radiolucent material.

A blade adjustment system 250 is configured to change a spacing between the first blade 230 and the second blade 240. A handle 255 of the blade adjustment system 250 includes a pivotable coupling 256 allowing an orientation of a portion of the handle 255 to be changed. A drive element 252 extends along axis 112. An orientation of a proximal handle portion 255p p may be changed as indicated by axis 113. Flexibility in an orientation of part or all of the handle 25 may allow the user to adjust the handle 255 to a more comfortable handle orientation and may reduce the likelihood that the handle 255 blocks other movements of a user during surgery. In some embodiments, the handle 255 may have a location proximal to the working channel to facilitate access by a surgeon.

Figure 7:
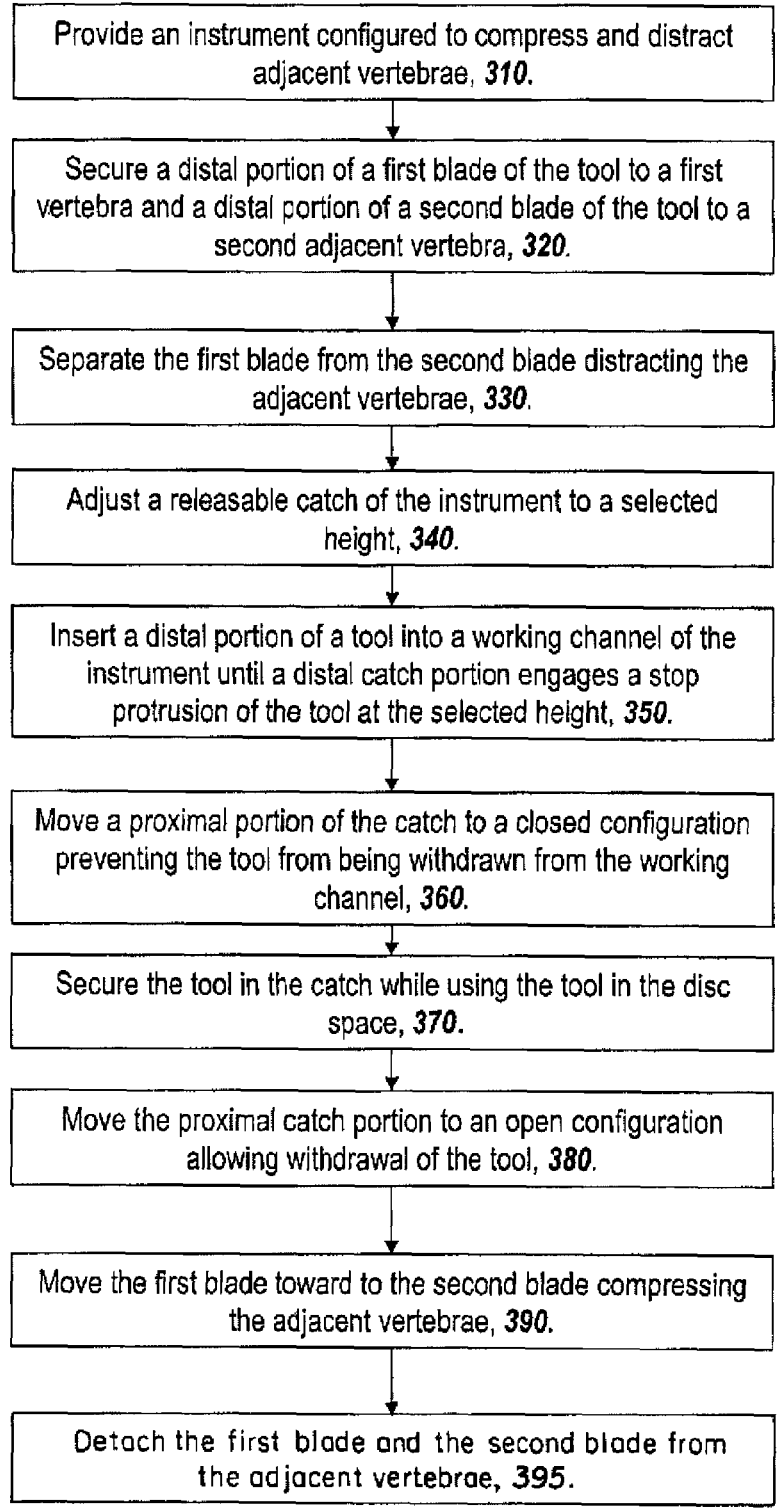
FIG. 7 is a flow chart illustrating a method of using the instrument to distract, compress and treat adjacent vertebrae, in accordance with another embodiment of the invention.

FIG. 7 is a flow chart of a method of manipulating adjacent vertebrae, in accordance with another embodiment of the invention. Method 300 is described with respect to exemplary instrument 10 and tool 210 solely for illustrative purposes. Method 300 may be performed with other instruments and other tools, as the invention is not limited in this respect.

Initially, an instrument 10 for distracting and/or compressing adjacent vertebrae is provided (step 310). The instrument 10 has a first blade 30, and a second blade 40, with a working channel 15 between the first blade 30 and the second blade 40, and an adjustment system 50. A distal portion of the first blade 30d is secured to a first vertebra and a distal portion of the second blade 40d is secured to a second vertebra that is adjacent to the first vertebra (step 320). The first blade 30 is separated from the second blade 40 thereby distracting the adjacent vertebrae (step 330).

A height of a releasable catch 72 of the depth stop system 70 is adjusted to a selected height $h_s$ (step 340). A distal portion of an associated tool 220 is inserted into the working channel 15 of the instrument until a stop element 122 of the associated tool 120 is engaged by a distal catch portion 72a of the releasable catch (step 350). An alignment element 80 of the instrument 10 may engage an alignment protrusion 124 of the tool 220 when a distal portion 220d of the tool 220 is inserted into the working channel 15 of the instrument. A proximal catch portion 72b of the depth stop system 70 is moved to a closed configuration preventing the tool 220 from being withdrawn from the working channel 15 (step 360). The associated tool is used with the stop element 122 of the tool 120 secured in the releasable catch 72 (step 370). After the tool is used, the proximal catch portion 72b may be moved to an open configuration allowing removal of the tool 120 (step 380). The first blade 30 may be moved toward the second blade 40 compressing the adjacent vertebrae (step 390). The first blade 30 and the second blade 40 may be detached from the adjacent vertebrae (step 395). The first blade 30 may be moved toward the second blade 40 with the first blade 30 and the second blade 40 detached from the adjacent vertebrae, which may allow easer withdrawal of the instrument from the subject.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. An instrument for distracting and/or compressing adjacent vertebrae, the instrument comprising:
   a yoke;
   a first blade movably mounted to the yoke;
   a second blade mounted to the yoke and opposed to the first blade, wherein the first blade, the second blade and the yoke form a working channel of the instrument, wherein at least one spinal fixation element extends from each of the first and second blades to securely anchor each of the first and second blades into respective vertebrae, wherein each blade includes at least one channel having a top opening and a bottom opening to allow the at least one spinal fixation element to be inserted from the top opening, along the channel, and out the bottom opening and into a vertebrae; and
   an adjustment system configured to adjust a spacing between the first blade and the second blade to distract or compress adjacent vertebrae when the first blade and the second blade have been securely anchored into the adjacent vertebrae by the respective spinal fixation elements, wherein the first blade and/or second blade are mounted for translational movement while maintaining an orientation of the first blade and second blade relative to each other, and wherein the spacing between the first blade and the second blade is adjusted by translating the first blade and/or second blade relative to each other to distract the adjacent vertebrae in a first mode of operation and compress the adjacent vertebrae in a second mode of operation.

2. The instrument of claim 1, wherein the first blade is slideably mounted to the yoke.

3. The instrument of claim 1, wherein the yoke comprises a pair of opposed guideways that each support the first blade and the second blade, and wherein each of the first blade and the second blade are disposed between the opposed guideways.

4. The instrument of claim 3, wherein a drive element of the adjustment system connects to a central portion of the first blade between the opposed guideways.

5. The instrument of claim 4, wherein the drive element is rotatably connected with the central portion of the first blade.

6. The instrument of claim 5, wherein the drive element is threaded and a central portion of the yoke has a threaded channel that engages the threads of the drive element.

7. The instrument of claim 3, wherein the adjustment system comprises a drive element aligned parallel to the opposed guideways.

8. The instrument of claim 1, further comprising an adjustable depth stop system configured to limit an insertion depth for an associated tool inserted into the working channel of the instrument.

9. The instrument of claim 1, further comprising at least one tool alignment element, each tool alignment element of the instrument configured to engage a corresponding alignment projection of an associated tool inserted into the working channel of the instrument.

10. The instrument of claim 1, wherein the second blade is fixedly mounted to the yoke.

11. The instrument of claim 1, wherein at least a portion of the first blade and at least a portion of the second blade comprise a radiolucent material.

12. An instrument for distracting and/or compressing adjacent vertebrae, the instrument comprising:
   a first blade and a second blade with a working channel therebetween, a spacing between the first blade and the second blade being selectively adjustable; and
   a depth stop system mounted to the instrument, the depth stop system is constructed to limit an insertion depth of an associated tool inserted into the working channel in an insertion direction, wherein the depth stop system engages the tool as it is inserted into the working channel in the insertion direction, the depth stop system including a releasable catch for securing a stop element of the associated tool, and wherein the instrument mounted depth stop system includes an adjustment system for adjusting the position of the releasable catch relative to the working channel between a first position and a second position to vary correspondingly the insertion depth of an associated tool between a first insertion depth and a second insertion depth when the associated tool is secured by the releasable catch.

13. The instrument of claim 12, wherein the depth stop system further comprises a depth stop lock configured to maintain a position of the releasable catch relative to the working channel.

14. The instrument of claim 12, wherein the releasable catch comprises:
   a distal catch portion configured to engage the stop element of the tool; and
   a proximal catch portion configured to allow insertion of the tool into the working channel of the distractor when the catch is in an open configuration, and configured to block withdrawal of the tool from the working channel of the distractor when the catch is in a closed configuration.

15. The instrument of claim 12, wherein the distractor further comprises an alignment element configured to engage a corresponding alignment protrusion of the tool.

16. The instrument of claim 15, wherein the alignment element is configured to block rotation, translation, and pivoting of the tool relative to the instrument.

17. The instrument of claim 15, wherein the first blade and the second blade are supported by a yoke.

18. An instrument for distracting and/or compressing adjacent vertebrae, the instrument comprising:
   a yoke;
   a first blade movably mounted to the yoke;
   a second blade mounted to the yoke and opposed to the first blade, wherein the first blade, the second blade and the yoke form a working channel of the instrument, wherein at least one spinal fixation element extends from each of the first and second blades to securely anchor each of the first and second blades into respective vertebrae, wherein each blade includes at least one channel having a top opening and a bottom opening to allow the at least one spinal fixation element to be inserted from the top opening, along the channel, and out the bottom opening and into a vertebrae; and
   means for adjusting a spacing between the first blade and the second blade when the first blade and the second blade have been securely anchored into adjacent vertebrae by the respective spinal fixation elements to distract or compress the adjacent vertebrae, wherein the first blade and/or second blade are mounted for translational movement while maintaining an orientation of the first blade and second blade relative to each other, and wherein the spacing between the first blade and the second blade is adjusted by translating the first blade and/or second blade relative to each other to distract the adjacent vertebrae in a first mode of operation and compress the adjacent vertebrae in a second mode of operation.

19. The instrument of claim 18, further comprising:
   means for limiting an insertion depth of an associated tool inserted into the working channel;
   means for adjusting the limit for the insertion depth; and
   means for securing the associated tool to the instrument.

20. The instrument recited in claim 18, wherein the spinal fixation element is a bone screw.

21. The instrument recited in claim 1, wherein the spinal fixation element is a bone screw.

22. The instrument recited in claim 1, wherein the first blade and/or the second blade are constructed and arranged to be translated in parallel directions.

23. The instrument recited in claim 18, wherein the first blade and/or the second blade are constructed and arranged to be translated in parallel directions.

* * * * *